United States Patent
Zhou et al.

(10) Patent No.: US 11,492,316 B1
(45) Date of Patent: Nov. 8, 2022

(54) PRODUCTION METHOD AND PRODUCTION DEVICE OF HIGH-PURITY 1,6-HEXANEDIOL

(71) Applicant: Zhejiang Boju New Materials Co., Ltd., Lishui (CN)

(72) Inventors: Minghe Zhou, Lishui (CN); Bihong Xu, Lishui (CN); Jieyang Xu, Lishui (CN); Jun Zhou, Lishui (CN); Zhaochang Zhou, Lishui (CN)

(73) Assignee: Zhejiang Boju New Materials Co., Ltd.

( * ) Notice: Subject to any disclaimer, the term of this patent is extended or adjusted under 35 U.S.C. 154(b) by 0 days.

(21) Appl. No.: 17/833,156

(22) Filed: Jun. 6, 2022

(30) Foreign Application Priority Data

Jun. 7, 2021 (CN) .......................... 202110628298.0

(51) Int. Cl.
  *C07C 29/154* (2006.01)
  *C07C 67/08* (2006.01)
  *C07C 29/82* (2006.01)

(52) U.S. Cl.
  CPC ............ *C07C 29/154* (2013.01); *C07C 29/82* (2013.01); *C07C 67/08* (2013.01)

(58) Field of Classification Search
  CPC ........ C07C 29/82; C07C 29/154; C07C 67/08
  See application file for complete search history.

(56) References Cited

U.S. PATENT DOCUMENTS

| | | | |
|---|---|---|---|
| 6,288,286 B1 | 9/2001 | Stein et al. | |
| 6,313,358 B1 * | 11/2001 | Breitscheidel | C07C 67/60 568/864 |

(Continued)

FOREIGN PATENT DOCUMENTS

| | | |
|---|---|---|
| CA | 2247991 A1 | 9/1997 |
| CN | 1257470 A | 6/2000 |

(Continued)

OTHER PUBLICATIONS

CN109748778 (A), HuSong et al., Method for producing 1,6-hexanediol, English translation, 15 pages (Year: 2019).*

(Continued)

*Primary Examiner* — Yate' K Cutliff
(74) *Attorney, Agent, or Firm* — Lerner, David, Littenberg, Krumholz & Mentlik, LLP

(57) ABSTRACT

The present disclosure relates to the technical field of hexanediol production, and provides a production method and a production device of high-purity 1,6-hexanediol. A dipic acid and a $C_6$ mixed alcohol are mixed to conduct esterification to obtain a product feed liquid including an adipic acid diester, and the high-purity 1,6-hexanediol is obtained through hydrogenation reduction and distillation. In addition to being used as a reaction raw material, the $C_6$ mixed alcohol further acts as a water-carrying agent; water produced by the esterification is removed by azeotropy, thereby promoting a smooth reaction process to realize the esterification without a catalyst. The method does not need the catalyst during esterification, and the subsequent hydrogenation reduction can be directly conducted with no complicated post-treatment procedure required after the esterification. In addition, the method has simple preparation steps, recyclable $C_6$ mixed alcohol, less wastewater production, desirable environmental protection, and high product purity and yield.

8 Claims, 2 Drawing Sheets

(56) References Cited

U.S. PATENT DOCUMENTS

| | | |
|---|---|---|
| 6,407,294 B1 | 6/2002 | Breitscheidel et al. |
| 6,426,438 B1 | 7/2002 | Fischer et al. |
| 8,513,472 B2 * | 8/2013 | Li .................... C07C 29/149 568/903 |
| 2007/0112225 A1 | 5/2007 | Sirch et al. |
| 2008/0207958 A1 | 8/2008 | Haunert et al. |
| 2011/0201848 A1 | 8/2011 | Ii et al. |
| 2012/0059174 A1 | 3/2012 | Abillard et al. |

FOREIGN PATENT DOCUMENTS

| | | |
|---|---|---|
| CN | 1272835 A | 11/2000 |
| CN | 1302284 A | 7/2001 |
| CN | 1819982 A | 8/2006 |
| CN | 101265158 B | 5/2010 |
| CN | 102186798 A | 9/2011 |
| CN | 202246478 U | 5/2012 |
| CN | 106699567 B | 5/2019 |
| CN | 109748778 A | 5/2019 |
| CN | 110563553 A | 12/2019 |
| CN | 113683483 B | 5/2022 |
| WO | 2004046072 A1 | 6/2004 |

OTHER PUBLICATIONS

Search Report dated Dec. 30, 2021 from the Office Action for Chinese Application No. 202110628298.0 dated Jan. 6, 2022, 2 pages.

Wang, L. "Study on the Process of Preparation of 1,6-Hexanediol by Adipic Acid," Athesis submitted to Zhengzhou University, May 2013, pp. 1-131. [Providing English Translation of Abstract only].

* cited by examiner

PRODUCTION METHOD AND PRODUCTION DEVICE OF HIGH-PURITY 1,6-HEXANEDIOL

CROSS REFERENCE TO RELATED APPLICATION

This patent application claims the benefit and priority of Chinese Patent Application No. 202110628298.0, filed on Jun. 7, 2021, the disclosure of which is incorporated by reference herein in its entirety as part of the present application.

TECHNICAL FIELD

The present disclosure relates to the technical field of hexanediol production, in particular to a production method and a production device of high-purity 1,6-hexanediol.

BACKGROUND ART 1,6-hexanediol, as an environmental-friendly white solid at room temperature with a desirable chemical stability, is an important chemical raw material. The 1,6-hexanediol can be used in pharmaceutical synthesis and the preparation of advanced coatings, advanced inks, advanced resins, synthetic fiber rubbers, and surfactants.

In a traditional method, adipic acid and methanol are used as raw materials, and esterification is conduct under the action of a catalyst to generate an adipic acid diester, followed by conducting hydrogenation reduction to obtain the 1,6-hexanediol. This method requires a catalyst during the esterification, generally including inorganic acids, organic acids, acidic ionic liquids, and solid acidic resins. For example: in "Longfei Wang. *Research on the Process of Preparing 1,6-hexanediol from Adipic Acid* [D]. Zhengzhou University, 2013", esterification of adipic acid and methanol is conducted using a highly-acidic cation resin as a catalyst, the excessive methanol needs to be removed by pressure distillation, and the catalyst is separated; a crude product is neutralized, washed with water, and distilled under reduced pressure to obtain a finished product of dimethyl adipate; and the 1,6-hexanediol is prepared by hydrogenation reduction. In patent CN1302284A, the adipic acid and the methanol are subjected to esterification using sulfuric acid as a catalyst; the dimethyl adipate is prepared by post-treatment steps including anion exchange, distillation, and fractionation, and the 1,6-hexanediol is prepared by hydrogenation reduction. In patent CN106699567B, a catalyst is used, including: 2.5% of thionyl chloride, 1.2% of 4-dimethylaminopyridine, 1.5% of tin tetrachloride, and activated carbon making up to 100%. The adipic acid and the methanol are subjected to esterification with the above catalyst, and a crude dimethyl adipate product is distilled in a refining tower of a distillation column to obtain a qualified dimethyl adipate product. In patent CN101265158B, a solid acid catalyst, the adipic acid, and the methanol are mixed to conduct pre-esterification under normal pressure, and a supernatant of a pre-esterification reaction product is subjected to continuous esterification in a continuous esterification column with a methanol vapor under the catalyst, where the solid acid catalyst is highly-acidic ion exchange resin added at 1% to 10% of a mass of the adipic acid; after a reactant is purified by distillation, hydrogenation is conducted to obtain a crude alcohol, and the crude alcohol is purified by distillation to obtain the 1,6-hexanediol with a purity of 99.0%.

In the above solutions, the catalyst needs to be separated by post-treatment after the esterification, otherwise the catalyst in the subsequent hydrogenation reduction may be affected, causing poisoning of the catalyst easily to affect the product quality. In addition, after catalyst separation, tedious procedures such as recovery of the solvent methanol and distillation and purification of the adipic acid diester are required, with a relatively low product yield; moreover, the methanol recovery increases a production risk, generates a large amount of wastewater, and increases energy consumption. Furthermore, the traditional method produces a large amount of $C_6$ mixed alcohol by-products due to side reactions such as excessive hydrogenation and dehydration while preparing the 1,6-hexanediol; methyl cyclopentanol and cyclopentyl methanol in the mixed alcohol are difficult to be separated through general distillation procedures, and have a low market value.

SUMMARY

In view of this, the present disclosure provides a production method of high-purity 1,6-hexanediol. In the present disclosure, the 1,6-hexanediol is prepared by using a $C_6$ mixed alcohol as a raw material, which replaces methanol as a traditional raw material. The $C_6$ mixed alcohol has a boiling point higher than water, is insoluble in water, can form an azeotrope with water, and has a moderate reactivity; therefore, there is no need of a catalyst during the esterification, and hydrogenation reduction can be conducted directly after the esterification. Accordingly, the method has simple steps, low cost, and less emission of wastewater.

To achieve the above objective, the present disclosure provides the following technical solutions.

The present disclosure provides a production method of high-purity 1,6-hexanediol, including the following steps:

(1) mixing adipic acid with a $C_6$ mixed alcohol to conduct esterification without a catalyst to obtain an esterification product feed liquid; where an esterification product in the esterification product feed liquid is an adipic acid diester;

(2) introducing hydrogen into the esterification product feed liquid under the action of a catalyst to conduct hydrogenation reduction to obtain a crude 1,6-hexanediol product; and (3) conducting distillation on the crude 1,6-hexanediol product to obtain the high-purity 1,6-hexanediol and the $C_6$ mixed alcohol; and returning the $C_6$ mixed alcohol to step (1) to continue the esterification; where the $C_6$ mixed alcohol includes methyl cyclopentanol, cyclopentyl methanol, and n-hexanol; and during the esterification, an alcohol-water azeotrope produced by the esterification is separated and layered to obtain an alcohol, and the alcohol is returned to the esterification.

Preferably, the $C_6$ mixed alcohol may have 20% to 30% of the methyl cyclopentanol by mass percentage.

Preferably, the adipic acid and the $C_6$ mixed alcohol may have a weight ratio of 1:(2-4.5).

Preferably, the esterification may be conducted at 150° C. to 220° C., and terminated when a reaction solution has an acid value of less than or equal to 10 mg KOH/g.

Preferably, the esterification may be terminated when the reaction solution has the acid value of less than or equal to 5 mg KOH/g.

Preferably, the hydrogenation reduction may be conducted at 1 MPa to 20 MPa and 150° C. to 280° C.

Preferably, the catalyst may be a supported copper catalyst.

Preferably, the distillation may be conducted by continuous distillation in two columns; distillation in a first column is conducted at 10 mmHg to 25 mmHg and 100° C. to 150° C., and distillation in a second column is conducted at 8 mmHg to 20 mmHg and 150° C. to 200° C.; and a product of the distillation in the first column is the $C_6$ mixed alcohol, and a product of the distillation in the second column is the high-purity 1,6-hexanediol.

Preferably, the high-purity 1,6 hexanediol may have a purity of greater than or equal to 99%.

The present disclosure further provides a production device of high-purity 1,6-hexanediol, including an esterification reactor (1), where the esterification reactor (1) is provided with an inlet I, an alcohol-water azeotrope outlet and an esterification product feed liquid outlet;

an alcohol-water separator (2) has an inlet II communicated with the alcohol-water azeotrope outlet of the esterification reactor (1), the alcohol-water separator (2) is further provided with an alcohol outlet and a water outlet, and the alcohol outlet is communicated to the inlet I of the esterification reactor;

a hydrogenation reactor (3) has an inlet III communicated with the esterification product feed liquid outlet of the esterification reactor (1), and the hydrogenation reactor (3) is further provided with a hydrogen inlet and a crude 1,6-hexanediol product outlet;

a first distillation column (4) has an inlet IV communicated with the crude 1,6-hexanediol product outlet of the hydrogenation reactor (3), the first distillation column (4) is further provided with a column top outlet and a column reactor outlet, and the column top outlet is communicated with the inlet I of the esterification reactor (1); and a second distillation column (5) has an inlet V communicated with the column reactor outlet of the first distillation column (4), and the second distillation column (5) is further provided with a high-purity 1,6-hexanediol outlet at a column top and a high-boiling component outlet at a column reactor.

The present disclosure provides a production method of high-purity 1,6-hexanediol. In the present disclosure, adipic acid and a $C_6$ mixed alcohol are mixed to conduct esterification to obtain a product feed liquid including dihexyl adipate, and the high-purity 1,6-hexanediol is obtained through hydrogenation reduction and distillation. During the esterification, in addition to being used as a reaction raw material, the $C_6$ mixed alcohol further acts as a water-carrying agent; water produced by the esterification is removed from the reactor by azeotropy, thereby promoting a smooth reaction process to realize the esterification without a catalyst. In addition, cyclopentyl methanol in the raw material $C_6$ mixed alcohol is difficult to form esters due to steric hindrance, and can be separated during the esterification and the water removal by azeotropy. The cyclopentyl methanol can be used as a pharmaceutical intermediate, and as a fragrance and a plasticizer, thereby increasing a market added value of by-products $C_6$ monohydric alcohols. The method does not need the catalyst, and the subsequent hydrogenation reduction can be directly conducted with no complicated post-treatment procedure required or purification by distillation on the intermediate product adipic acid diester after the esterification, which means a simple preparation process and low cost. In addition, the $C_6$ mixed alcohol is a by-product generated during producing the 1,6-hexanediol by a traditional method, realizing resource utilization of the $C_6$ mixed alcohol and further reducing a production cost of the 1,6-hexanediol.

The method does not need the steps of water washing, catalyst separation, solvent recovery, and esterification product purification after the esterification, and has a high product yield, and low wastewater discharge. Meanwhile, the alcohol in an alcohol-water mixture produced by azeotropy in the esterification is separated and returned to the esterification, and the $C_6$ mixed alcohol produced in distillation of the crude 1,6-hexanediol product is also returned to the esterification. This realizes the recycling of $C_6$ mixed alcohol, further reduces the wastewater generated in the whole process, and has desirable environmental protection and high utilization rate of alcohol.

During the hydrogenation reduction of the method, since there is a small amount of a raw material $C_6$ mixed monohydric alcohol in the intermediate product adipic acid diester as a hydrogenation raw material, the production of new by-product $C_6$ alcohol can be suppressed in the hydrogenation reduction, thereby improving selectivity and product yield of the product 1,6-hexanediol.

The results of examples show that the production method of the present disclosure can obtain 1,6-hexanediol with a purity reaching not less than 99% and a molar yield up to not less than 95%.

The present disclosure further provides a production device of high-purity 1,6-hexanediol. The device can obtain the high-purity 1,6-hexanediol.

DETAILED DESCRIPTION OF THE EMBODIMENTS

Figure 1:
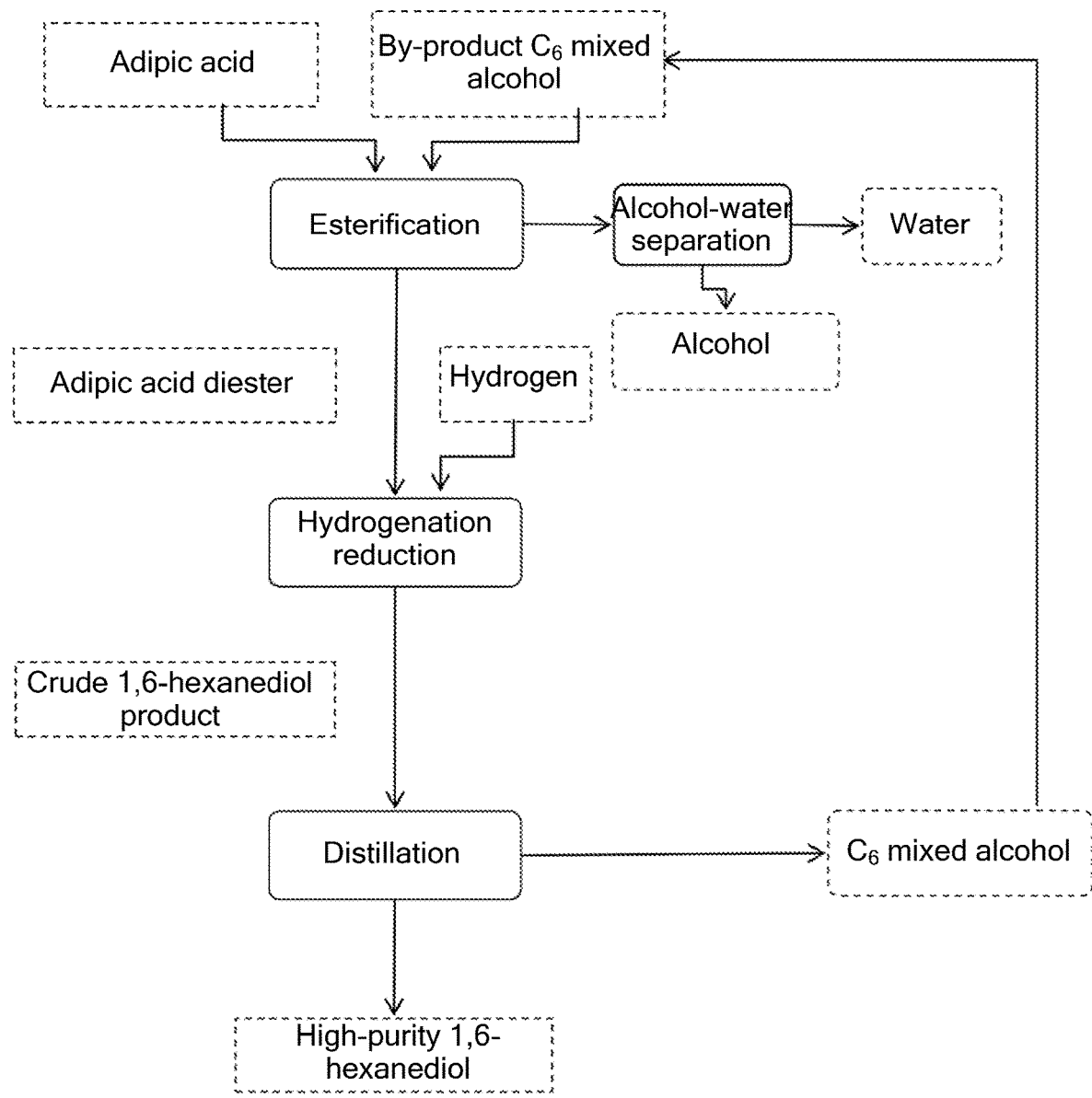
FIG. 1 shows a process flow diagram of a production method of high-purity 1,6-hexanediol provided by the present disclosure.

The present disclosure provides a production method of high-purity 1,6-hexanediol. A process flow diagram of the production method is shown in FIG. 1, and is described in detail below with reference to FIG. 1.

The present disclosure provides a production method of high-purity 1,6-hexanediol, including the following steps:

(1) mixing adipic acid with a $C_6$ mixed alcohol to conduct esterification without a catalyst to obtain an esterification product feed liquid; where an esterification product in the esterification product feed liquid is an adipic acid diester;

(2) introducing hydrogen into the esterification product feed liquid under the action of a catalyst to conduct hydrogenation reduction to obtain a crude 1,6-hexanediol product; and (3) conducting distillation on the crude 1,6-hexanediol product to obtain the high-purity 1,6-hexanediol and the $C_6$ mixed alcohol; and returning the $C_6$ mixed alcohol to step (1) to continue the esterification; where the $C_6$ mixed alcohol includes methyl cyclopentanol, cyclopentyl methanol, and n-hexanol; and during the esterification, an alcohol-water azeotrope produced by the esterification is separated and layered to obtain an alcohol, and the alcohol is returned to the esterification.

In the present disclosure, the adipic acid is mixed with the $C_6$ mixed alcohol to conduct esterification without a catalyst to obtain the esterification product feed liquid. In the present disclosure, the $C_6$ mixed alcohol is preferably a by-product obtained when the 1,6-hexanediol is prepared by a traditional method, and the $C_6$ mixed alcohol includes methyl cyclopentanol, cyclopentyl methanol and n-hexanol; in the $C_6$ mixed alcohol, the methyl cyclopentanol has a mass percentage of preferably 20% to 30%, more preferably 22% to 28%; the cyclopentyl methanol has a mass percentage content of preferably 5% to 20%, and the n-hexanol has a mass percentage content of preferably 20% to 40%; and in the $C_6$ mixed alcohol, the methyl cyclopentanol, the cyclopentyl methanol, and the n-hexanol have a total mass percentage of about 80% to 90%, with cyclopentanol as a balance.

In the present disclosure, the adipic acid and the $C_6$ mixed alcohol have a weight ratio of preferably 1:(2-4.5), more preferably 1:(2.5-4); the esterification is conducted preferably in an esterification reactor at preferably 150° C. to 220° C., and terminated when a reaction solution has an acid value of preferably less than or equal to 10 mg KOH/g, more preferably less than or equal to 5 mg KOH/g. During the esterification, the methyl cyclopentanol, the cyclopentyl methanol, and the n-hexanol in the $C_6$ mixed alcohol each undergo esterification with the adipic acid to produce corresponding adipic acid diesters; a product in the esterification product feed liquid is dihexyl adipate, and the dihexyl adipate specifically includes di(methylcyclopentyl)adipate, di(cyclopentylmethyl)adipate, and the dihexyl adipate.

Taking the cyclopentyl methanol as an example, an equation of the esterification is shown in formula I:

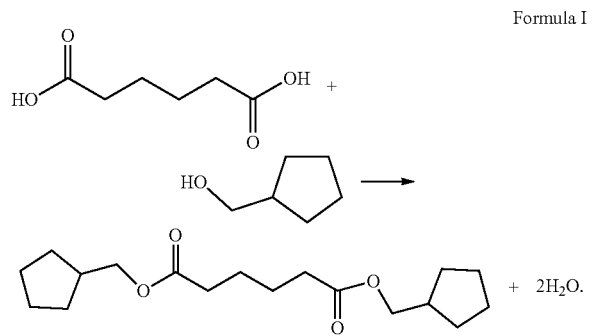

Formula I

In the present disclosure, in addition to being used as a reaction raw material, the $C_6$ mixed alcohol further acts as a water-carrying agent. The methyl cyclopentanol has the optimal water-carrying properties, and esterification produces water to conduct azeotropy with the $C_6$ mixed alcohol; an alcohol-water mixture produced by azeotropy is preferably separated from the esterification reactor by a water separation device; the $C_6$ mixed alcohol has poor water solubility, the separated alcohol-water mixture is layered to obtain the alcohol and water, and the separated alcohol is preferably returned to the esterification reactor to continue to participate in the reaction. By the water-carrying effect of $C_6$ mixed alcohol, the esterification without a catalyst is realized by designing a reaction process.

In the present disclosure, hydrogen is introduced into the esterification product feed liquid under the action of a catalyst to conduct hydrogenation reduction to obtain the crude 1,6-hexanediol product. The hydrogenation reduction is preferably conducted in a hydrogenation reaction column; after the esterification, there is unreacted excessive alcohol in the esterification product feed liquid. It is found that the alcohol present in the esterification product feed liquid does not affect the hydrogenation reduction; and since alcohol by-products are produced during the hydrogenation reduction, a small amount of the alcohol in the esterification product feed liquid can also inhibit the generation of by-product alcohols, thereby improving the selectivity of 1,6-hexanediol. Therefore, after the esterification, no treatment is required, and the product feed liquid is directly added to the hydrogenation reaction column.

In the present disclosure, the catalyst is preferably a supported copper catalyst; there is no special requirement for the supported copper catalyst, and supported copper catalysts having a catalytic effect on the hydrogenation reduction and well known to those skilled in the art can be used; specifically, commercially-available products can be purchased, or products are prepared using methods well known to those skilled in the art. In a specific example, the supported copper catalyst has a carrier of preferably $\gamma\text{-Al}_2\text{O}_3$, and active components of preferably CuO and ZnO; the CuO has a loading capacity of preferably 5 wt % to 40 wt %, more preferably 10 wt % to 30 wt %, and the ZnO has a loading capacity of preferably 5 wt % to 30 wt %, more preferably 8 wt % to 20 wt %; the supported copper catalyst is prepared preferably by equivalent-volume impregnation, specifically including: impregnating the $\gamma\text{-Al}_2\text{O}_3$ in a mixed solution of copper nitrate and zinc nitrate, followed by drying and roasting in sequence to obtain the supported copper catalyst; where the roasting is conducted at preferably 400° C. to 600° C.

In the present disclosure, preferably, the catalyst is packed in the hydrogenation reaction column, the esterification product feed liquid is added, and hydrogen is introduced for the reaction.

In the present disclosure, the hydrogenation reduction is conducted at preferably 1 MPa to 20 MPa, more preferably 3 MPa to 18 MPa and preferably 150° C. to 280° C., more preferably 180° C. to 260° C.; preferably, the adipic acid diester in the hydrogenation reduction has a conversion rate controlled to be not less than 99%; during the hydrogenation reduction, the adipic acid diester generates the 1,6-hexanediol; taking the di(cyclopentylmethyl)adipate as an example, an reaction formula of the hydrogenation reduction is shown in formula II:

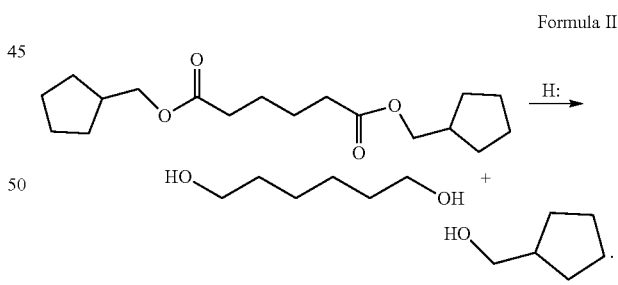

Formula II

In the present disclosure, the crude 1,6-hexanediol product includes the 1,6-hexanediol, the $C_6$ mixed alcohol (mainly including methyl cyclopentanol, cyclopentyl methanol, and n-hexanol) and a small amount of a $C_5$ alcohol (mainly including cyclopentanol) and a small amount of an adipic acid monoester by-product; the adipic acid diester has a selectivity to hexanediol reaching not less than 98%.

In the present disclosure, distillation is conducted on the crude 1,6-hexanediol product to obtain the high-purity 1,6-hexanediol and the $C_6$ mixed alcohol. In the present disclosure, the distillation is conducted preferably by continuous distillation in two columns; distillation in a first column is conducted at preferably 10 mmHg to 25 mmHg, more preferably 15 mmHg to 20 mmHg and 100° C. to 150° C., more preferably 110° C. to 140° C., and distillation in a second column is conducted at preferably 8 mmHg to 20 mmHg, more preferably 10 mmHg to 15 mmHg and 150° C. to 200° C., more preferably 160° C. to 180° C.; and a product of the distillation in the first column is the $C_6$ mixed alcohol, and the $C_6$ mixed alcohol preferably returns to the esterification reactor to continue reaction; a product of the distillation in the second column is the high-purity 1,6-hexanediol, and the high-purity 1,6-hexanediol has a purity of not less than 99%, specifically not less than 99.7%. A column reactor of the second column produces a high-boiling fraction adipic acid monoester, and the adipic acid monoester can be recycled as an esterification raw material.

Figure 2:
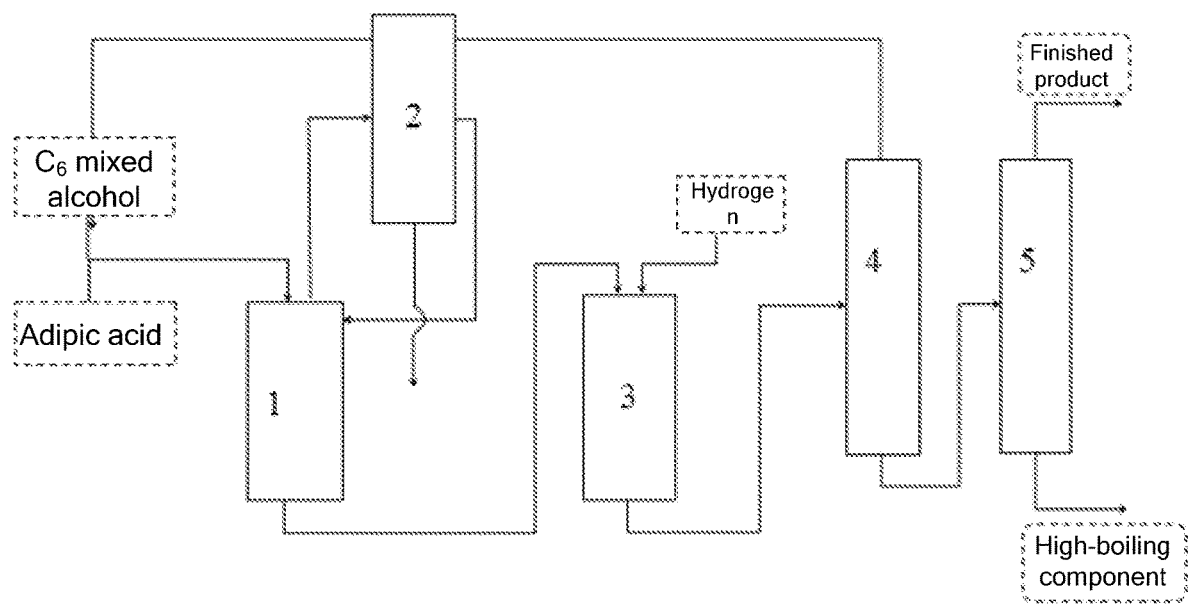
FIG. 2 shows a schematic diagram of a production device of high-purity 1,6-hexanediol provided by the present disclosure, where 1 refers to an esterification reactor, 2 refers to an alcohol-water separator, 3 refers to a hydrogenation reactor, 4 refers to a first distillation column, and 5 refers to a second distillation column.

The present disclosure further provides a production device of high-purity 1,6-hexanediol, including an esterification reactor (1), an alcohol-water separator (2), a hydrogenation reactor (3), a first distillation column (4), and a second distillation column (5). A schematic diagram of the production device is shown in FIG. 2, and a specific description is given below in conjunction with FIG. 2.

In the present disclosure, the device includes an esterification reactor (1), where the esterification reactor (1) is provided with an inlet I, an alcohol-water azeotrope outlet, and an esterification product feed liquid outlet, and the inlet I is used for adding the adipic acid and the $C_6$ mixed alcohol; the alcohol-water azeotrope outlet is preferably arranged at a top of the esterification reactor, and the esterification product feed liquid outlet is preferably arranged at a bottom of the esterification reactor.

In the present disclosure, the device further includes an alcohol-water separator (2) having an inlet II communicated with the alcohol-water azeotrope outlet of the esterification reactor (1), where the alcohol-water separator (2) is provided with an alcohol outlet and a water outlet, and the alcohol outlet is communicated with the inlet I of the esterification reactor; the alcohol-water separator (2) is used to separate an alcohol-water azeotrope produced by the esterification, and a separated alcohol returns to the esterification reactor to continue to participate in the reaction.

In the present disclosure, the device further includes a hydrogenation reactor (3) having an inlet III communicated with the esterification product feed liquid outlet of the esterification reactor (1), and the hydrogenation reactor (3) is further provided with a hydrogen inlet and a crude 1,6-hexanediol product outlet. The hydrogenation reactor is used for hydrogenating the adipic acid diester in the esterification product feed liquid; and the hydrogenation reactor (3) is filled with the supported copper catalyst.

In the present disclosure, the device further includes a first distillation column 4 having an inlet IV communicated with the crude 1,6-hexanediol product outlet of the hydrogenation reactor (3); the first distillation column (4) is further provided with a column top outlet and a column reactor outlet, and the column top outlet is communicated with the inlet I of the esterification reactor (1).

In the present disclosure, the device further includes a second distillation column (5) having an inlet V communicated with the column reactor outlet of the first distillation column (4), and the second distillation column (5) is further provided with a high-purity 1,6-hexanediol outlet at a column top and a high-boiling component outlet at a column reactor.

In the present disclosure, the device is used to prepare the high-purity 1,6-hexanediol using the $C_6$ mixed alcohol. Description is conducted in detail below in conjunction with FIG. 2: the $C_6$ mixed alcohol and the adipic acid are added into the esterification reactor (1) to conduct esterification; during the esterification, the produced alcohol-water azeotrope enters the alcohol-water separator (2) for alcohol-water separation, the separated alcohol is returned to the esterification reactor (1), and the separated water is discharged from the alcohol-water separator; the esterification reaction feed liquid in the esterification reactor (1) enters the hydrogenation reactor (3) to conduct hydrogenation to obtain the crude 1,6-hexanediol product; the crude 1,6-hexanediol product enters the first distillation column for distillation, and the $C_6$ mixed alcohol is obtained at the column top; the $C_6$ mixed alcohol is returned to the esterification reactor (1) and continues to participate in the reaction, and the product of the first distillation column enters the second distillation column to continue distillation; and in the second distillation column, the high-purity 1,6-hexanediol product is obtained at the column top, and the high boiling component is obtained at the column reactor.

The technical solutions in the present disclosure are clearly and completely described below in conjunction with examples of the present disclosure.

Example 1

A $C_6$ mixed alcohol was provided. The $C_6$ mixed alcohol was a by-product of producing 1,6-hexanediol by a traditional method, where methyl cyclopentanol had a mass percentage of 30%, cyclopentyl methanol had a mass percentage of 30%, and n-hexanol had a mass percentage of 20%; the high-purity 1,6-hexanediol was prepared using a device shown in FIG. 2, where specific preparation steps were as follows:

1) Esterification was conducted on adipic acid and the $C_6$ mixed alcohol in an esterification reactor (1); during the esterification, an alcohol-water mixture produced by azeotropy entered an alcohol-water separator (2) for alcohol-water separation, and a separated alcohol was returned to the esterification reactor (1); when a reaction solution had an acid value of less than 10 mg KOH/g, the reaction was terminated.

2) A product feed liquid obtained in step (1) was introduced into a hydrogenation reactor 3 equipped with a supported copper catalyst (with a carrier of $\gamma$-$Al_2O_3$ and active components of CuO and ZnO, where the CuO had a loading capacity of 25 wt %, the ZnO had a loading capacity of 15 wt %, and the catalyst was reduced before use), and hydrogen was introduced into the reactor to conduct hydrogenation reduction; during the reaction, a conversion rate of an adipic acid diester in the hydrogenation reduction was detected and controlled to be greater than or equal to 99%; by detecting a content of hexanediol in a product, it was known that the adipic acid diester during the hydrogenation had a selectivity of greater than or equal to 98%.

3) A crude 1,6-hexanediol product obtained in step (2) was subjected to continuous distillation in two columns, where a first distillation column (4) had a pressure of 10 mmHg and a temperature of 120° C., and a second distillation column (5) had a pressure of 15 mmHg and a temperature of preferably 180° C.; a column top product of the first distillation column (4) was the $C_6$ mixed alcohol, the $C_6$ mixed alcohol was returned to the esterification reactor (1) to continue the reaction, and a column top product of the second distillation column (5) is 1,6-hexanediol.

The consumption of adipic acid and $C_6$ mixed alcohol, the esterification temperature, and the pressure and temperature of hydrogenation reduction were specifically shown in Table 1; and purity and yield of the 1,6-hexanediol were shown in Table 1.

Examples 2-11

Other conditions were the same as those in Example 1, only consumption of adipic acid and $C_6$ mixed alcohol, the esterification temperature, and the pressure and temperature of hydrogenation reduction were changed, specifically shown in Table 1; and purity and yield of the 1,6-hexanediol were shown in Table 1.

TABLE 1

Reaction conditions and product purity and yield of Examples 1 to 11

| Item | Adipic acid dosage/kg | $C_6$ mixed alcohol dosage/kg | Esterification temperature/ °C. | Hydrogenation reduction pressure/MPa | Hydrogenation reduction temperature/°C. | Product purity | Product molar yield |
|---|---|---|---|---|---|---|---|
| Example 1 | 500 | 1000 | 220 | 1 | 280 | 99.76% | 95.02% |
| Example 2 | 500 | 1125 | 212 | 3 | 260 | 99.86% | 95.08% |
| Example 3 | 500 | 1250 | 205 | 5 | 245 | 99.85% | 95.11% |
| Example 4 | 500 | 1375 | 198 | 6 | 235 | 99.80% | 95.02% |
| Example 5 | 500 | 1500 | 190 | 9 | 225 | 99.81% | 95.05% |
| Example 6 | 500 | 1625 | 182 | 12 | 210 | 99.87% | 95.12% |
| Example 7 | 500 | 1750 | 175 | 13 | 200 | 99.92% | 95.52% |
| Example 8 | 500 | 1875 | 168 | 15 | 185 | 99.86% | 95.23% |
| Example 9 | 500 | 2000 | 160 | 17 | 175 | 99.91% | 95.19% |
| Example 10 | 500 | 2125 | 158 | 18 | 165 | 99.88% | 95.16% |
| Example 11 | 500 | 2250 | 150 | 20 | 150 | 99.75% | 95.06% |

According to the data in Table 1, it can be seen that the 1,6-hexanediol obtained by the preparation method of the present disclosure has a purity of not less than 99.7% and a yield of not less than 95%.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A production method of high-purity 1,6-hexanediol, comprising the following steps:
   (1) mixing adipic acid with a $C_6$ mixed alcohol to conduct esterification without a catalyst to obtain an esterification product feed liquid; wherein an esterification product in the esterification product feed liquid is an adipic acid diester;
   (2) introducing hydrogen into the esterification product feed liquid under the action of a catalyst to conduct hydrogenation reduction to obtain a crude 1,6-hexanediol product; and
   (3) conducting distillation on the crude 1,6-hexanediol product to obtain the high-purity 1,6-hexanediol and the $C_6$ mixed alcohol; and returning the $C_6$ mixed alcohol to step (1) to continue the esterification; wherein the high-purity 1,6 hexanediol has a purity of greater than or equal to 99.7%;
   the $C_6$ mixed alcohol comprises methyl cyclopentanol, cyclopentyl methanol, and n-hexanol; the $C_6$ mixed alcohol has 20% to 30% of the methyl cyclopentanol by mass percentage, 5% to 20% of the cyclopentyl methanol by mass percentage, and 20% to 40% of the n-hexanol by mass percentage; the adipic acid and the $C_6$ mixed alcohol have a weight ratio of 1:(2-4.5); and during the esterification, an alcohol-water azeotrope produced by the esterification is separated and layered to obtain an alcohol, and the alcohol is returned to the esterification.

2. The production method according to claim 1, wherein the esterification is conducted at 150° C. to 220° C., and terminated when a reaction solution has an acid value of less than or equal to 10 mg KOH/g.

3. The production method according to claim 1, wherein the esterification is terminated when the reaction solution has the acid value of less than or equal to 5 mg KOH/g.

4. The production method according to claim 1, wherein the hydrogenation reduction is conducted at 1 MPa to 20 MPa and 150° C. to 280° C.

5. The production method according to claim 1, wherein the catalyst is a supported copper catalyst.

6. The production method according to claim 1, wherein the distillation is conducted by continuous distillation in two columns; distillation in a first column is conducted at 10 mmHg to 25 mmHg and 100° C. to 150° C., and distillation in a second column is conducted at 8 mmHg to 20 mmHg and 150° C. to 200° C.; and a product of the distillation in the first column is the $C_6$ mixed alcohol, and a product of the distillation in the second column is the high-purity 1,6-hexanediol.

7. The production method according to claim 2, wherein the esterification is terminated when the reaction solution has the acid value of less than or equal to 5 mg KOH/g.

8. The production method according to claim 4, wherein the catalyst is a supported copper catalyst.

* * * * *